United States Patent [19]

Cohen et al.

[11] 4,071,459
[45] Jan. 31, 1978

[54] ALKYL-GUANIDINO-HETEROCYCLIC COMPOUNDS, THEIR MANUFACTURE AND USE AS ADDITIVES FOR FUELS AND LUBRICANTS

[75] Inventors: Choua Cohen; Bernard Sillion, both of Grenoble, France

[73] Assignee: Institut Francais du Petrole, Rueil-Malmaison, France

[21] Appl. No.: 608,966

[22] Filed: Aug. 29, 1975

[30] Foreign Application Priority Data

Sept. 10, 1974 France .................. 74 30819

[51] Int. Cl.² .............................................. C10M 1/32
[52] U.S. Cl. ..................................... 252/50; 252/47; 252/47.5; 252/51.5 R; 260/564 A; 548/335
[58] Field of Search ............ 252/50, 47, 47.5, 51.5 R; 260/309.2, 564 A

[56] References Cited

U.S. PATENT DOCUMENTS

| | | | |
|---|---|---|---|
| 2,373,021 | 4/1945 | Downing et al. ................ | 252/50 X |
| 2,754,183 | 7/1956 | Chenicek et al. ................ | 252/50 X |
| 2,783,210 | 2/1957 | Kennerly ........................ | 252/50 X |
| 2,933,502 | 4/1960 | Klopping ...................... | 260/309.2 X |
| 2,987,522 | 6/1961 | Shen ............................ | 260/309.2 X |
| 3,364,220 | 1/1968 | Biel et al. ...................... | 260/326.8 X |
| 3,454,555 | 7/1969 | van der Voort et al. ......... | 252/50 X |
| 3,655,560 | 4/1972 | Andress ........................ | 252/50 |
| 3,740,338 | 6/1973 | Allphin et al. ................. | 252/51.5 R X |
| 3,950,333 | 4/1976 | Durant et al. .................. | 260/309.2 X |

*Primary Examiner*—Herbert Levine
*Assistant Examiner*—Andrew H. Metz
*Attorney, Agent, or Firm*—Millen & White

[57] ABSTRACT

Alkyl-guanidino heterocyclic compound produced by alkylation with a halogenated hydrocarbon of the general formula $RX_n$, of a guanidino-heterocyclic compound (A) of general formula:

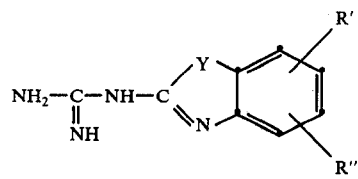

in which R is substantially a hydrocarbon radical containing about 10 to 200 carbon atoms, X is a halogen atom and n is 1 or 2; Y is an oxygen atom, —O—, a sulfur atom —S—, a —NH— group, or a —COHN— group in which the carbon atom is directly bound to the benzene ring, R' and R" are each a hydrogen atom, an alkyl radical having from 1 to 10 carbon atoms, or a —Z—Ar group in which Z is a divalent atom or group and Ar is a substituted or unsubstituted aromatic radical, R' and R" being capable of forming together, when they are in ortho position, an aliphatic or aromatic cycle fused to the benzene ring.

17 Claims, No Drawings

ALKYL-GUANIDINO-HETEROCYCLIC COMPOUNDS, THEIR MANUFACTURE AND USE AS ADDITIVES FOR FUELS AND LUBRICANTS

This invention concerns alkyl-guanidino-heterocyclic compounds, their manufacture and use as additives, particularly for motor fuels and lubricants.

The compounds of the invention are useful as dispersing agents, detergents and, more particularly, as additives for lubricating compositions, motor fuels, hydrocarbon oils and power transmission fluids.

One of the main problems concerning crankcase oils is that the unavoidable presence therein of metal particles, carbonaceous products, decomposition products resulting from the degradation of fuel and oil, and water, leads to the formation of sludges, which are particularly detrimental to a good operation of the engine.

It is known that the use of detergent additives such as metal phenates and sulfonates, makes it possible to maintain the particles in suspension and, consequently, to avoid the formation of sludges. But these "basic" detergents are efficient mainly at high temperatures and are not so well adapted to the operating conditions of the engine when the car is used over short distances (particularly in town traffic, for the so-called "stop-and-go" driving), which are insufficient for bringing the oil to a high temperature. In order to solve the problem of such a type of use of a car, in which during a substantial portion of the running time of this engine, the temperature is lower than the optimal temperature, it has been suggested to make use of ashless additives. However, these additives are not efficient at high temperatures and their thermal stability is low.

A major purpose of the invention is to provide efficient detergent and dispersing lubricating compositions for use in engines operated at either low or high temperatures and/or, alternately, low and high temperatures.

Moreover, it is known that the use of antipollution devices in the fuel feeding circuits (for example devices for recycling the crankcase gases) results in the formation of deposits in the carburetor and the induction manifold system. In order to solve this problem, a certain number of detergent additives for gasoline have been proposed which act both as surface active agents (by fixing on metal surfaces, they prevent deposits thereon) and by their dissolving power with respect to the deposits already formed on the walls. It has been observed that these products are efficient only on the cold walls of the induction circuit and that they do not prevent deposits on hot walls, particularly in the induction chambers.

One of the main objects of the invention is also to provide an improved fuel composition the use of which does not result in the formation of deposits in the induction circuit.

The applicant has found new organic compounds, i.e. alkyl-guanidino-heterocyclic compounds, which have sufficient thermal stability and surfactant properties to result in a detergent action both in crankcase oils and in gasolines, even in contact with hot surfaces.

The present invention concerns:
new organic compounds consisting of alkyl-guanidino-heterocyclic compounds;
their process of manufacture;
their use as detergent-dispersing additives in the oils;
their use as detergent additives in fuels;
the lubricating compositions containing them, and
the fuel compositions containing them.

The alkyl-guanidino-heterocyclic compounds according to the invention are defined as resulting, as a general rule, from the alkylation, with a halogenated hydrocarbon $RX_n$, of guanidino-heterocyclic compounds of the general formula:

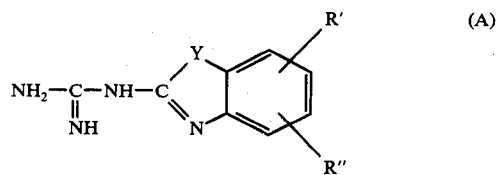

In the formula $RX_n$ of the halogenated hydrocarbon, R is a saturated or unsaturated substantially hydrocarbon radical containing about 10 to 200 carbon atoms, and which may further contain polar atoms or groups in proportions which do not alter its hydrocarbon nature, for example, oxygen atoms —O—, carbonyl groups or halogen atoms; X is a halogen atom, for example chlorine, bromine or iodine and n is an integer, generally 1 or 2.

In the formula of the guanidino-heterocyclic compound (A), Y may be:

an oxygen atom —O—: in this case the heterocycle is a benzoxazole;

a sulfur atom —S—: in this case the heterocycle is a benzothiazole;

a —NH— group: in this case the heterocycle is a benzimidazole;

a —CONH— group in which the carbon atom is directly bound to the benzene ring: in this case the heterocycle is a 4-quinazolone;

R′ andR″ may be a hydrogen atom, or an alkyl radical having from 1 to 10 carbon atoms; when they are in ortho positions, R′ and R″ may also form together a ring fused to the benzene ring, this ring being either aliphatic or aromatic; R′ and R″ may also represent a —Z— Ar group in which Z is an oxygen atom, a sulfur atom or a divalent aliphatic group, such as:

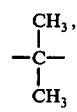

radical such as a phenyl radical or a substituted aromatic radical such as an alkyl-phenyl radical in which the alkyl group contains from 1 to 10 carbon atoms.

The halogenated hydrocarbons $RX_n$ involved in the invention, are preferably derived from substantially saturated petroleum cuts, or from polymers of α-olefins or of internal olefins. As examples of such hydrocarbon substances, we can mention: petroleum waxes, 1-polybutenes, polyisobutenes, 2-polybutenes, 3-polypentenes, copolymers of isobutene and butadiene, copolymers of isobutene and chloroprene and copolymers of 1-butene, 2-butene and isobutene. In view of the solubility in oil and of the stability of the resulting alkyl-guanidino heterocyclic compound, it is preferable that R be substantially aliphatic and saturated.

Among the halogenated hydrocarbons $RX_n$, we make use in most cases, for the obvious purpose of reducing the cost, of chlorinated compounds. They can be prepared from the corresponding hydrocarbon compounds, by any usual chlorination method. Thus, for example, we can proceed to the injection of a chlorine stream into the hydrocarbon maintained at a temperature of about 20° to 100° C, in the optional presence of a solvent for dissolving the hydrocarbons of high molecular weight.

The guanidino-heterocyclic compounds of the general formula (A) embraced in the present invention may be obtained in a known manner by reacting dicyandiamide with hydrochlorides of the corresponding substituted anilines (B) according to the following reaction scheme:

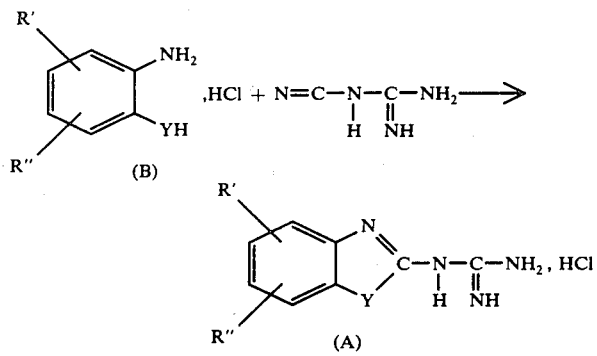

in which Y, R', R" are defined as above. The reaction proceeds easily at water or ethanol reflux, the compounds (A) being obtained in the form of hydrochlorides, then liberated by the action of a strong base such as soda and optionally recrystallized.

It is known in the art to prepare some simple guanidino-heterocyclic compounds. Thus, for example, G. Pelizzari has described in Gaz. Chem. Ital. 51-1 140 (1921) the preparation of guanidino-benzimidazole (Y = NH and R' = R" = H) from orthophenylene diamine. R. M. Acheson et al. have described, in Nature 160, 53 (1947) and J. Chem. Soc. 1948, 1366–71, the guanadino-benzimidazoles in which R' = Cl, $CH_3O$- or $CH_3$- and R" = H.

The preparation of guanidino-benzoxazole (Y = —O— and R' = R" = H) from aminophenol is described by Smith et al. in J; Am. Chem. Soc. 51,2522 (1929).

The preparation of guanidino-benzothiazole (Y = —S— and R' = R" = H) from aminothiophenol is described by Toriso Takahashi et al. in Pharm. Soc. Japan 63, 249–52 (1943).

The preparation of 2-guanidino (3H) 4-quinazolone

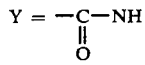

and R' = R" = H), from anthranilic acid, is described by Barbara Skowronska-Serafinowa et al. in Roczniki Chem. 26, 51–7 (1952).

The preparation of the alkyl-guanidino-heterocylic compounds of the invention, is performed by reacting halogenated hydrocarbons, mainly the chlorinated ones, such as hereabove defined, with guanidino-heterocyclic compounds of the corresponding general formula (A).

The ratio of the two reactants may vary for example from 0.7 to 2.5 moles of compound (A) per halogen atom of the halogenated hydrocarbon; preferably, a ratio close to 1/1 is used.

The reaction is performed at a temperature from 100° to 250° C, generally over a period from a few minutes to several hours, in most cases from 15 minutes to 6 hours.

In most cases, the operation is conducted without solvent, but it may be useful to add a solvent in some cases, for example when the medium is too viscous for being conveniently stirred.

The reaction proceeds easily without catalyst, but as it is accompanied with evolution of halohydric acid, for example hydrochloric acid, it may be favored by the addition of a captor, sodium carbonate being often used since it liberates carbon dioxide and gives an inert precipitate of sodium halide (for example chloride) which can be separated by filtration at the end of the reaction. Other captors, such for example as calcium oxide or sodium hydroxide, are also very efficient. In addition, in order to facilitate the operation, it may be convenient to dilute the reaction medium by means of oil or of a hydrocarbon, depending on the use to which the product is destined, in order to obtain directly, after filtration, a concentrated solution in oil (use as detergent — dispersing additive for oil) or in said hydrocarbon (use as detergent additive for fuel). The reaction for producing alkyl-guanidino-heterocyclic compounds of the invention may be advantageously conducted in the reactor where is carried out the chlorination of the starting hydrocarbon and subsequently thereto.

The resulting products have an infra-red spectrum showing the disappearance of the halogencarbon bonds and the elementary analysis shows a very small halogen content (for example chlorine) of about 10 to 15% of the initial value and a nitrogen proportion of about 40 to 100% of the theoretical one (corresponding to the fixation of one heterocycle per halogen atom of the halogenated hydrocarbon involved in the reaction).

The alkyl-guanidino heterocyclic compounds of the invention, used as detergent and/or dispersing additives for lubricants and fuels are added thereto in sufficient proportions for imparting them the desired properties. These proportions may be, for example, from 1 to 10% by weight in lubricants and from 0.002 to 0.1% by weight in fuels.

The following examples illustrate the invention.

EXAMPLE 1

In a glass reactor, provided with a stirrer, shaped as an anchor, and heated in an oil bath, we prepared various compounds of the invention (designated under references Ia to Ig), by reacting, under nitrogen scavenging, chlorinated poly-isobutenes with 2-guanidino benzimidazole (A) in the presence of sodium carbonate, at the conditions reported in table I, below.

TABLE I

| | Chlorinated Polyisobutene | | | (A) Wt. (g) | Car- bona- te (g) | Reaction | | Final Product | |
|---|---|---|---|---|---|---|---|---|---|
| Ref. | M (1) | Cl % Wt. | Wt. (g) | | | Dur- at- ion (h) | Tem- pera- ture (° C) | N % b.w | Cl % b.w |
| I a | 950 | 3.66 | 10 | 4.37 | 1 | 4 | 190 | 2.7 | 0.4 |
| I b | 1280 | 2.7 | 12.8 | 4.37 | 1 | 4 | 200 | 2.3 | 0.45 |
| I c | 480 | 8.04 | 18 | 8.74 | 2 | 4 | 200 | 5.1 | 0.6 |
| I d | 980 | 4.3 | 10 | 4.37 | 1 | 4 | 200 | 3.2 | 0.4 |
| I e | 950 | 3.66 | 10 | 2.2 | 1 | 8 | 200 | 3 | 0.35 |
| I f | 950 | 3.66 | 2 | 0.84 | 0.2 | 2 | 250 | 3 | 0.4 |
| I g | 960 | 4 | 460 | 200 | 48 | 4 | 200 | 1.4 | 0.2 |

(1) M is the molecular weight of the chlorinated polyisobutene.

Products Ia to If have been diluted with hexane after reaction, filtered with a filtration aid and then evaporated.

Product Ig has been diluted with 470 g of a 100 N oil at the end of the reaction and then filtered. The nitrogen and Cl contents mentioned for Ig have been determined on the obtained solution.

EXAMPLE 2

By operating as in example 1, there is reacted 255 g of chlorinated polyisobutene having a molecular weight of 950 and containing 3.66% by weight of chlorine, with 112 g of 2-guanidino benzoxazole and 25 g of sodium carbonate for 4 hours at 200° C. The reaction medium is diluted with hexane, filtered and hexane is evaporated therefrom. The resulting product (product II) contains 3.4% by weight of nitrogen and 0.5% b.w. of chlorine.

EXAMPLE 3

While operating as in example 1, there is a reacted 70 g of chlorinated polyisobutene having a molecular weight of 950 and a chlorine content of 3.66% by weight, with 30 g of 2-guanidino benzothiazole and 7.4 g of sodium carbonate, for 4 hours at 200° C.

The reaction medium is diluted with hexane, filtered and hexane evaporated therefrom.

The resulting product (product III) contains 5.25% by weight of nitrogen and 0.2% b.w. of chlorine.

EXAMPLE 4

While operating as in example 1, there is a reacted 300 g of chlorinated polyisobutene having a chlorine content of 3.66% by weight and a molecular weight of 950, with 152 g of 2-guanidino (3H) 4-quinazolone and 32 g of sodium carbonate for 4 hours at 200° C. The reaction medium is diluted with hexane, filtered, and hexane evaporated therefrom. The resulting product (product IV) contains 4.5% b.w. of nitrogen and 0.6% b.w. of chlorine.

EXAMPLE 5

The dispersing power of lubricating compositions containing certain additives prepared as described in the preceding examples have been tested by examination of spots obtained on a filter paper after deposition thereon of a drop of used mineral oil containing 2% b.w. of additive. In strictly identical operating conditions we have determined, in each case, the ratio of the average diameter of the black spot to the average diameter of the oil aureole. The higher this ratio, the better the dispersing power of the additive. The results obtained are reported in table II below, in which are also mentioned the results of identical tests conducted without additive and with 2% of an additive available in the trade (alkenylsuccinimide).

TABLE II

| Additive | Naught | Commercial | Ib | Ic | Ig | II | III | IV |
|---|---|---|---|---|---|---|---|---|
| 25° C | 0.4 | 0.60 | 0.67 | 0.54 | 0.65 | 0.56 | 0.62 | 0.58 |
| 150° C | 0.30 | 0.48 | 0.54 | 0.46 | 0.58 | 0.43 | 0.51 | 0.50 |

The detergent property of product Ig, added in a proportion of 2% b.w. to a lubricating oil, has been tested on a Petter AV1 engine according to method AT4 and on a Petter AV1 engine according to method DEF. We have obtained respectively a merit over 100 of 94 and a merit over 10 of 9.4, which is a remarkable result.

EXAMPLE 6

The detergent power of the fuel compositions containing certain additives prepared as in examples 1 to 4, has been examined in a so-called "Induction system deposit" test according to standard MIL-G-3056 C. According to this test, a mixture of gasoline and air is pulverized on a metal test piece at 200° C in well defined conditions and thereafter the deposit formed on the test piece is weighed. For each test we made use of 100 cc of gasoline containing 80 ppm of used oil and 200 ppm of the additive to be tested. The results are given in Table III below.

TABLE III

| ADDITIVE | NOUGHT | I a | I c | II | III | IV |
|---|---|---|---|---|---|---|
| Deposit (mg) | 6.1 | 0 | <1 | <1 | 0 | 0 |

These results show that the detergent power of the additives is such that they make it possible to avoid or at least to considerably decrease the deposits due to gasoline and oil.

We have tested product Ic as detergent additive at a concentration of 100 ppm in gasoline, in a test of carburetor clogging. The total merit obtained over 10 was 7.5, which is a very satisfactory result.

We claim:
1. An alkyl-guanidino heterocyclic compound produced by alkylation at 100°-250° C. with a halogenated hydrocarbon of the general formula $RX_n$, of a guanidino-heterocyclic compound (A) of the formula:

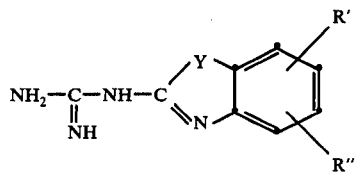

in which R is a hydrocarbon radical containing about 10 to 200 carbon atoms, X is a halogen atom and n is 1 or 2; Y is —NH—, R' and R" are each a hydrogen atom, or an alkyl radical having from 1 to 10 carbon atoms, or a —Z—Ar group in which Z is —O—, —S—, or alkylene and Ar is aromatic hydrocarbyl or R' and R" together, when they are in ortho position, represent a carbocyclic ring fused to the benzene ring, the proportion of the reactants being 0.7-2.5 moles of (A) per gm. atom of halogen in $RX_n$.

2. A compound according to claim 1, in which the radical R of the halogenated hydrocarbon $RX_n$ is substantially aliphatic and saturated.

3. A compound according to claim 2 in which the halogenated hydrocarbon $RX_n$ is derived from a substantially saturated petroleum cut or from an olefin polymer.

4. A compound according to claim 2, in which the halogenated hydrocarbon $RX_n$ is a chlorinated hydrocarbon.

5. A compound according to claim 4, in which the halogenated hydrocarbon $RX_n$ is a chlorinated polyisobutene.

6. A compound according to claim 1 in which compound (A) is 2-guanidino benzimidazole.

7. A compound according to claim 6, wherein said halogenated hydrocarbon is a chlorinated polyisobutene having a molecular weight of 1280 and 2.7 weight percent of Cl.

8. A compound according to claim 6, wherein said halogenated hydrocarbon is a chlorinated polyisobutene having a molecular weight of 960 and 4 weight percent of Cl 9. A lubricating composition comprising a major amount of a mineral oil, and in a sufficient proportion to obtain dispersing properties at least one compound according to claim 1.

10. A lubricating composition according to claim 9, in which said proportion is from 1 to 10% by weight.

11. A lubricating composition comprising a major amount of a mineral oil, and in a sufficient proportion to obtain dispersing properties at least one compound according to claim 6.

12. A lubricating composition comprising a major amount of a mineral oil, and in a sufficient proportion to obtain dispersing properties at least one compound according to claim 2.

13. A lubricating composition comprising a major amount of a mineral oil, and in a sufficient proportion to obtain dispersing properties at least one compound according to claim 3.

14. A lubricating composition comprising a major amount of a mineral oil, and in a sufficient proportion to obtain dispersing properties at least one compound according to claim 4.

15. A lubricating composition comprising a major amount of a mineral oil, and in a sufficient proportion to obtain dispersing properties at least one compound according to claim 5.

16. A lubricating composition comprising a major amount of a mineral oil, and in a sufficient proportion to obtain dispersing properties at least one compound according to claim 7.

17. A lubricating composition comprising a major amount of a mineral oil, and in a sufficient proportion to obtain dispersing properties at least one compound according to claim 8.

* * * * *

UNITED STATES PATENT AND TRADEMARK OFFICE
CERTIFICATE OF CORRECTION

PATENT NO. : 4,071,459
DATED : January 31, 1978
INVENTOR(S) : CHOUA COHEN ET AL

It is certified that error appears in the above-identified patent and that said Letters Patent are hereby corrected as shown below:

Column 2, lines 42-49: reads "atom or a divalent aliphatic group, such as:

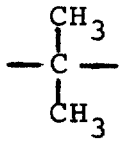

radical such as a phenyl radical or a substituted aro-"

should read -- atom or a divalent aliphatic group, such as: $-CH_2-$; $-(CH_2)_4-$ or

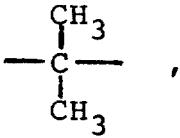

and AR is a simple aromatic radical such as a phenyl radical or a substituted aro- -- .

Signed and Sealed this

Thirtieth Day of October 1979

[SEAL]

Attest:

RUTH C. MASON
*Attesting Officer*

LUTRELLE F. PARKER
*Acting Commissioner of Patents and Trademarks*